US00PP14754P2

(12) United States Plant Patent
Zary

(10) Patent No.: US PP14,754 P2
(45) Date of Patent: May 4, 2004

(54) FLORIBUNDA ROSE PLANT NAMED 'JACBEAU'

(50) Latin Name: *Rosa hybrida*
Varietal Denomination: JACbeau

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 0 days.

(21) Appl. No.: 10/300,567

(22) Filed: Nov. 19, 2002

(51) Int. Cl.[7] ..... A01H 5/00
(52) U.S. Cl. ..... Plt./144
(58) Field of Search ..... Plt./144, 141, 103, Plt./133, 145

*Primary Examiner*—Bruce R. Campell
*Assistant Examiner*—June Hwu
(74) *Attorney, Agent, or Firm*—Klarquist Sparkman, LLP

(57) ABSTRACT

Floribunda rose plant characterized particularly by its constant flowering with ivory flowers having a yellow base in trusses of 3 to 5 blooms and its deep maroon new foliage that turns dark green.

1 Drawing Sheet

Genus and species: Rosa hybrida.
Variety denomination: 'JACbeau'.

SUMMARY OF THE INVENTION

The present invention relates to a new and distinct variety of rose plant named 'JACbeau' of the floribunda class which was originated by me by crossing the variety 'JACjem,' U.S. Plant Pat. No. 5,001, with the variety 'JACdew,' U.S. Plant Pat. No. 5,122.

BACKGROUND OF THE INVENTION

The primary objective of this breeding was to produce a new rose variety having the compact habit, profuse blooming and good disease resistance of the female parent combined with good disease resistance and well branched habit of the male parent.

BRIEF SUMMARY OF THE INVENTION

The objective was substantially achieved, along with other desirable improvements, as evidenced by the following unique combination of characteristics that are outstanding in the new variety and that distinguish it from its parents, as well as from all other varieties of which I am aware:

1. Constant flowering during the growing season;
2. Resistant to powdery mildew and rust;
3. Compact, well-branched plant habit;
4. Deep maroon colored new foliage that turns dark green; and
5. Flowers produced in trusses of 3 to 5.

Asexual reproduction of this new variety by budding, as performed at Wasco, Calif., shows that the foregoing and all other characteristics and distinctions come true to form and are established and transmitted through succeeding propagations.

COMPARISON WITH PARENTS

'JACbeau' is different in flower color to both parents, 'JACjem' having medium yellow flowers, 'JACdew' having orange-red flowers.

COMPARISON WITH SIMILAR VARIETY

'JACbeau' has a unique cream colored bud opening to an ivory or near white flower with a yellow base making this rose unlike any other. It is more compact than 'KORbin' (not patented) and more cream colored than 'JACare,' U.S. Plant Pat. No. 6,515), the two closest varieties.

BRIEF DESCRIPTION OF THE ILLUSTRATION

The accompanying illustration shows typical specimens of the vegetative growth and flowers of this new variety in different stages of development, depicted in color as nearly true as it is reasonably possible to make the same in a color illustration of this character.

DETAILED BOTANICAL DESCRIPTION

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'JACjem' (U.S. Plant Pat. No. 5,001).
*Pollen parent.*—'JACdew' (U.S. Plant Pat. No. 5,122).

FLOWER

Observations made from plants beginning at two years of age grown in a garden environment at Somis, Calif., January–December 2001.

Blooming habit: Continuous.
Bud:
*Size.*—About 30 mm long when the petals start to unfurl.
*Form.*—The bud form is long, pointed ovoid.
*Color.*—When sepals first divide, bud color is Yellow-White Group 158B. When half blown, the upper sides of the petals are Yellow-White Group 158D; and the lower sides of the petals are Yellow-White Group 158C.

*Sepals.*—Color: Upper Surface: Predominantly Green Group 138A, often with a center streak of Yellow-Green Group 146D. Lower Surface: Green Group 139B. Length: 32–38 mm. Width: 9–11 mm. Overall Shape: Obovate. Apex: Acuminate. Surface texture: Hoary. There are three normally appendaged sepals. There are two unappendaged sepals with hairy edges.

*Receptacle.*—Color: Green Group 139B often with Greyed Purple Group 183B in areas exposed to bright sunlight. Shape: Funnel. Size: Medium, about 11 mm×9 mm. Surface: Glabrous.

*Peduncle.*—Length: Medium, about 60–70 mm. Surface: Glandular. Color: Green Group 139B often with Greyed-Purple Group 183B in areas exposed to bright sun. Strength: Stiff, erect.

Bloom:

*Size.*—Large. Average open size is 100 mm.

*Borne.*—Several together in clusters of 3–5 blooms having a flat shape.

*Stems.*—Strength: Strong. Average length is about 250 mm.

*Form.*—When first open: High centered. Permanence: Flattens.

*Petalage.*—Number of petals under normal conditions: 20–25.

*Color.*—The upper sides of the petals are Yellow-White Group 158D. The reverse sides of the petals are Yellow-White Group 158C. The base of each petal has a small (5 mm×5 mm) Yellow Group 5D color spot on both surfaces. The major color on the upper side is Yellow-White Group 158D.

*Variegations.*—None.

*Discoloration.*—The general tonality at the end of the first day: No change. At the end of the third day: No change.

*Fragrance.*—Moderate. Character of fragrance: Fruity.

Petals:

*Texture.*—Thick.

*Shape.*—Round.

*Margin.*—Smooth, but undulate.

*Apex shape.*—Rounded to slightly murconulate.

*Base shape.*—Rounded.

*Size.*—Width: 4 cm. Length: 5 cm.

*Form.*—Flat.

*Arrangement.*—Imbricated.

*Petaloids.*—None.

*Persistence.*—Petals drop off cleanly before drying.

*Lastingness.*—On the plant: Fair (about 6 days). As a cut flower: Fair (about 7 days).

Reproductive parts:

*Stamens.*—Number: 100–120. Length: 8–16 mm. Anthers: Length: 1.5–2 mm. Color: Yellow-Orange Group 15B. Arrangement: Regular around styles. Filaments: Color: Yellow Group 12C with Red Group 47C. Length: 6–14 mm. Pollen: Color: None observed.

*Pistils.*—Number: 80–100. Styles: Color: Red Group 47B. Length: 5–7 mm. Stigmas: Color: Greyed-Yellow Group 161C. Length: 0.75–1 mm.

*Hips.*—Color: Green Group 139B. Size: 15 mm×15 mm. Shape: Round.

*Seeds.*—None observed.

Plant:

*Form.*—Bush.

*Growth.*—Vigorous, upright, branching.

*Age to maturity.*—Two years.

*Mature plant.*—Height: 100 cm. Width: 80 cm.

*Rootstock.*—Dr. Huey.

Foliage: Nunber of leaflets on normal mid-stem leaves: 5.

*Size.*—Large (140 mm long×140 mm wide).

*Quantity.*—Abundant.

*Color.*—New foliage: Upper side: Greyed-Purple Group 187A. Lower side: Greyed-Purple Group 187A. Old foliage: Upper side: Green Group 136A. Lower side: Green Group 136C.

Leaflets:

*Size.*—About 70 mm long×40 mm wide.

*Shape.*—Pointed oval.

*Base shape.*—Slightly oblique.

*Apex shape.*—Acuminate.

*Texture.*—Upperside: Leathery, glossy.

*Edge.*—Serrated.

*Serrations.*—Single.

*Petiole.*—Color: Green Group 137C, often with some Greyed-Purple Group 183B at the point of attachment.

*Petiole rachis.*—Color: Green Group 137C. Underside: Rough with prickles and with some glands.

*Stipules.*—Length: 20 mm. Surface: Smooth, but with some glands. Color: Green Group 137C, the center being Greyed-Purple 183B.

*Disease resistance.*—Resistant to mildew and rust. Susceptible to blackspot under normal growing conditions.

*Pest resistance.*—Not tested.

*Vein color.*—Green Group 137C.

*Venation pattern.*—Reticulate.

Wood:

*New wood.*—Color: Greyed-Purple Group 183B. Bark: Smooth.

*Old wood.*—Color: Green Group 137B. Bark: Smooth.

Prickles:

*Quantity.*—On main canes from base: Ordinary. On laterals from main canes: Ordinary.

*Form.*—Hooked downward.

*Length.*—8–10 mm.

*Color when young.*—Greyed-Purple Group 183A.

*Color when mature.*—Greyed-Orange Group 177C.

Small prickles:

*Quantity.*—On main stalks: None. On laterals: None.

Winter hardiness: Hardy to Zone 5.

I claim:

1. A new and distinct variety of rose plant of the floribunda class, substantially as herein shown and described, characterized particularly by its constant flowering with ivory flowers having a yellow base in trusses of 3 to 5 blooms and its deep maroon new foliage that turns dark green.

* * * * *

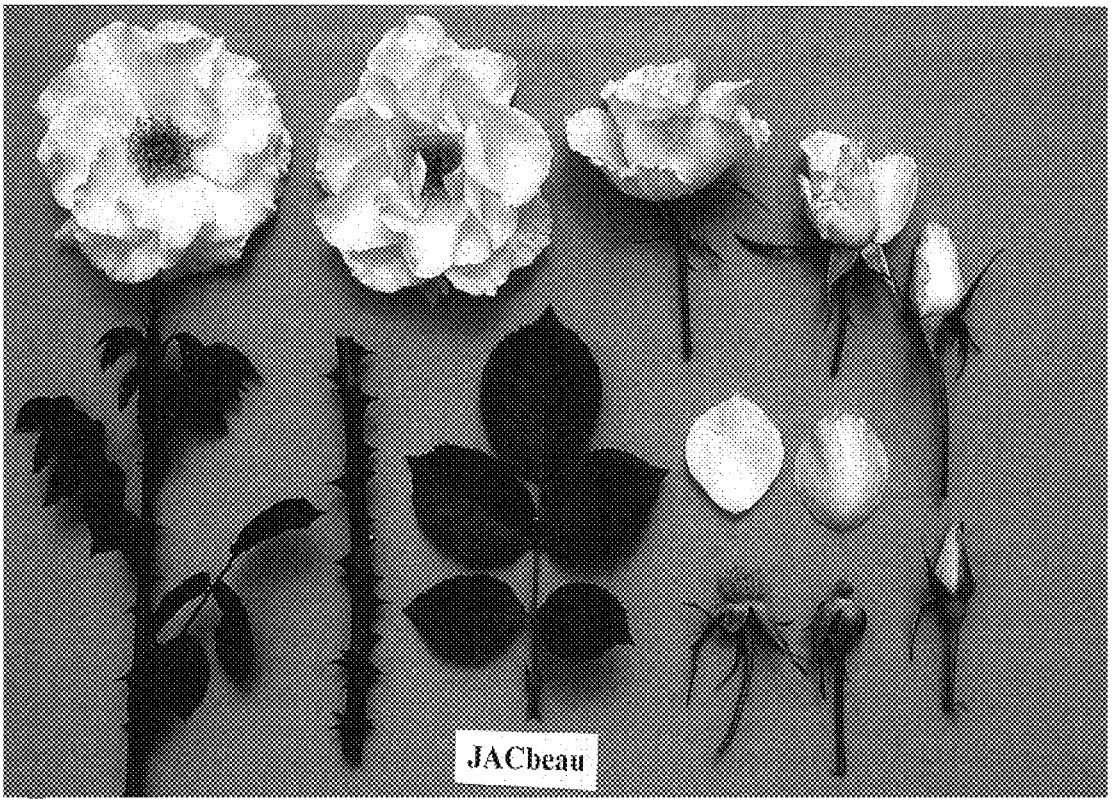
JACbeau